(12) United States Patent
Daniel et al.

(10) Patent No.: US 7,997,121 B2
(45) Date of Patent: Aug. 16, 2011

(54) MILLIWAVE MELTER MONITORING SYSTEM

(75) Inventors: William E. Daniel, North Augusta, SC (US); Paul P. Woskov, Bedford, MA (US); Shanmugavelayutham K. Sundaram, Richland, WA (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 525 days.

(21) Appl. No.: 12/218,086

(22) Filed: Jul. 11, 2008

(65) Prior Publication Data

US 2010/0008395 A1 Jan. 14, 2010

(51) Int. Cl.
 *G01N 11/02* (2006.01)
(52) U.S. Cl. ......... 73/54.01; 73/54.02; 374/126; 356/44
(58) Field of Classification Search ................ 73/54.01; 374/126; 356/44
 See application file for complete search history.

(56) References Cited

U.S. PATENT DOCUMENTS

| | | |
|---|---|---|
| 4,521,861 A | 6/1985 | Logan et al. |
| 4,568,200 A | 2/1986 | Hatono et al. |
| 4,673,298 A | 6/1987 | Hunter et al. |
| 4,693,614 A | 9/1987 | Hatono et al. |
| 4,979,134 A | 12/1990 | Arima et al. |
| 5,255,286 A | 10/1993 | Moslehi et al. |
| 5,468,964 A | 11/1995 | Gopalsami et al. |
| 5,564,830 A * | 10/1996 | Bobel et al. ............ 374/126 |
| 5,573,339 A | 11/1996 | Woskov et al. |
| 5,785,426 A | 7/1998 | Woskov et al. |
| 6,172,367 B1 | 1/2001 | Fritz et al. |
| 6,414,606 B1 | 7/2002 | Yujiri et al. |
| 6,682,216 B1 | 1/2004 | Small, IV et al. |
| 7,152,007 B2 | 12/2006 | Arnone et al. |

FOREIGN PATENT DOCUMENTS

| | | |
|---|---|---|
| CN | 1405330 A | 8/2001 |
| JP | 2006029869 | 2/2006 |
| KR | 2004022676 A | 9/2002 |

OTHER PUBLICATIONS

Woskov, Machuzak, Thomas, Sundaram and Daniel; Millimeter-Wave Monitoring of Nuclear Waste Glass Melts—an Overview; Environmental issues and Waste Management Technologies VII, Ceramic Transactions, vol. 132; 2002; pp. 189-201; (13 pages).

Woskov, Sundaram, Daniel and Miller; Molten Salt Dynamics in Glass Melts using Millimeter-Wave Emissivity Measurements; Non Crystalline Solids; vol. 341/1-3, 21-25; 2004; (17 pages).

Woskov, Sundaram and Daniel; Waste Glass Melter Process Monitoring with Millimeter Waves; ANS Spectrum meeting in Reno Nevada; 2002; pp. 1-6; (6 pages).

Woskov, Sundaram, Daniel and Miller; Millimeter-Wave Measurements of Nuclear Waste Glass Melts; IRMMW MMW meas; Unknown Date; (2 pages).

Woskov and Sundaram; Thermal Return Reflection Method for Resolving Emissivity and Temperature in Radiometric Methods; Journal of Applied Physics, vol. 92, pp. 6302-6310; Dec. 2002; (33 pages).

* cited by examiner

*Primary Examiner* — Hezron Williams
*Assistant Examiner* — Paul West
(74) *Attorney, Agent, or Firm* — Bennett Mullinax, LLC

(57) ABSTRACT

A milliwave melter monitoring system is presented that has a waveguide with a portion capable of contacting a molten material in a melter for use in measuring one or more properties of the molten material in a furnace under extreme environments. A receiver is configured for use in obtaining signals from the melt/material transmitted to appropriate electronics through the waveguide. The receiver is configured for receiving signals from the waveguide when contacting the molten material for use in determining the viscosity of the molten material. Other embodiments exist in which the temperature, emissivity, viscosity and other properties of the molten material are measured.

20 Claims, 2 Drawing Sheets

MILLIWAVE MELTER MONITORING SYSTEM

STATEMENT AS TO RIGHTS TO INVENTIONS MADE UNDER FEDERALLY SPONSORED RESEARCH AND DEVELOPMENT

This invention was made with Government support under Contract No. DE-AC09-96-SR18500 awarded by the United States Department of Energy. The Government has certain rights in the invention.

FIELD OF THE INVENTION

The present invention relates generally to a milliwave melter monitoring system that may use millimeter-wavelength electromagnetic radiation for obtaining measurements of a high-temperature process. A particular exemplary embodiment of the present application is related to a milliwave melter monitoring system employed in a glass melter for use in measuring melt parameters such as temperature, emissivity, foaming, surface displacement, viscosity, specific gravity and noble metal accumulation.

BACKGROUND

Electrically (Joule)-heated glass melters are used for the vitrification of nuclear waste. Due to the lack of on-line monitoring and capable measurement equipment, current processes rely on predictive models validated by more laboratory/melter testing with simulants but limited testing with actual radioactive wastes to predict and control the conversion process. Predictive modeling necessitates a more costly, conservative operation in order to take into account uncertainties in the process such as foaming, crystal formation, noble metals build-up, and salt layer formation. Additionally, predictive modeling will become more difficult in the future as waste glass chemistry evolves with changes in waste feed compositions and tank chemistries. Economical and environmental concerns thus dictate that improved methods of running this process be established.

Real-time measurements inside of a glass melter or other furnace are desirable in order to monitor performance of the furnace and to optimize the process. Presently, there are limited technological options. For example, infrared sensors may be employed in order to measure the temperature distribution within the furnace. Certain challenges exist, however, with such a measurement. The environment present within the furnace is often hot, smoky, and particle filled thus frustrating the ability of the infrared sensor to accurately measure temperature. Further, the temperature obtained from infrared sensors employed in furnaces may not be completely accurate since surface emissivity measurements are not acquired by the infrared sensors which are needed in order to accurately interpret temperatures. Additionally, as the black-body curve is non-linear in the IR region, sometimes two different emissivity values may be needed for certain ranges of temperature to measure it accurately.

Thermocouples can be used to obtain temperature inside of a furnace. However, the information obtained from these devices is limited to temperature data within the furnace and does not provide insight to other properties within the furnace for use in improving processing and performance. Further, the electrical wires associated with thermocouples have a limited heat/radiation tolerance and are prone to failure thus making their use in a furnace application less than ideal. Further, the thermocouple probe is not well suited for contacting certain materials to be measured, thus limiting their functionality in the furnace environment.

It is known to use a pyrometer with a single receiver in order to obtain temperature measurements within a furnace. Such known arrangements can employ a waveguide that is enclosed within a sleeve of alumina tubing. The end portion of the waveguide is located inside of the furnace and is easily replaceable in order to maintain performance due to its exposure to the harsh environment within the furnace. The waveguide is located away from material that is melted in the furnace, and the pyrometer is capable of obtaining limited information from the furnace such as temperature and emissivity, more often temperature, but not any other process parameters. Although capable of being used to obtain data from furnaces, the aforementioned arrangement is limited in the type of data that may be acquired for use in optimizing the measured process. Accordingly, there remains room for variation and improvement within the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which.

Figure 1:
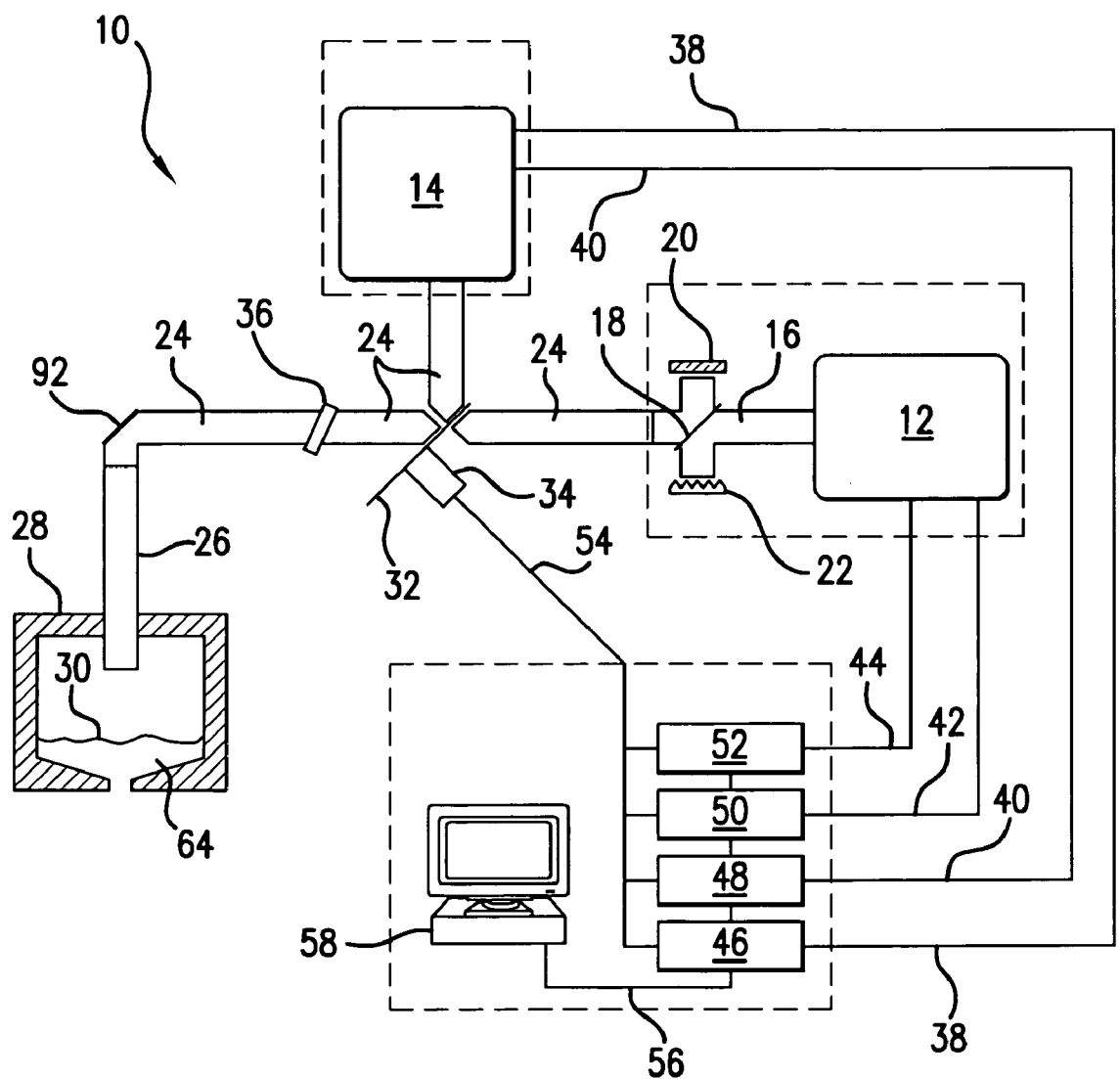
FIG. 1 is a schematic view of a milliwave melter monitoring system in accordance with one exemplary embodiment.

Repeat use of reference characters in the present specification and drawings is intended to represent the same or analogous features or elements of the invention.

DETAILED DESCRIPTION

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for a milliwave melter monitoring system 10 using millimeter-wavelength electromechanical radiation that is configured for use in obtaining measurements from a glass melter 28. The system 10 may have a waveguide 26 that is located inside of the melter 28 in order to obtain data regarding conditions therein such as temperature and emissivity. The waveguide 26 is also configured for being immersed within molten material 64 present within the melter 28 in order to acquire additional information such as viscosity, specific gravity, and noble metals build-up. The system 10 may also feature a pair of milliwave melter monitoring heterodyne receivers 12 and 14 for real time monitoring of the multiple melt properties. The use of multiple receivers 12 and 14 may allow for the capture of transient events that have implications in the overall process so that the employed process can be monitored and optimized simultaneously. Although shown as including a pair of receivers 12 and 14, it is to be understood that from two to ten receivers may be employed in the system 10 in accordance with other exemplary embodiments.

An exemplary embodiment of a milliwave melter monitoring system 10 in accordance with one exemplary embodiment of the present invention is shown in FIG. 1. Here, the system 10 includes a pair of milliwave melter monitoring heterodyne receivers 12 and 14. Receiver 12 is configured as a thermal return reflection receiver 12, and receiver 14 is arranged so as to be a passive receiver 14 in the system 10. The receivers 12 and 14 are capable of observing conditions within a melter 28 through signals received from one or more waveguides that extend from the receivers 12 and 14 to the melter 28.

A crossed waveguide 16 is mounted in front of the receiver 12 and has a beam splitter 18. The beam splitter 18 functions to divide (approximately equally) the signal moving towards the receiver 12 so that part of the signal is directed at a side mirror 20 positioned adjacent the crossed waveguide 16. The remaining portion of the signal continues on to the receiver 12. The signal directed at the side mirror 20 is bounced off of the side mirror 20 and continues back to the portion of the melter 28 being viewed such as a monitored surface 30. In this manner, a portion of the signal is thus used to probe the monitored surface 30. A milliwave melter monitoring signal dump 22 is located adjacent the crossed waveguide 16 at a position opposite the side mirror 20. The signal dump 22 is used in order to trap the portion of the redirected signal that is not returned by the beam splitter 18. The signal dump 22 also functions to prevent interference in the system 10 by ending the portion of the receiver 12 view that is reflected by the beam splitter 18.

Additional waveguides 24 and 26 are present in the system 10 in order to direct the view of the receivers 12 and 14 to the monitored surface 30 and to transmit signals from the monitored surface 30 to the receivers 12 and 14. Although described as having three waveguides 16, 24 and 26, it is to be understood that any number may be present in accordance with various exemplary embodiments. For example, a single waveguide may be present in certain embodiments of the system 10, while up to ten waveguides may exist with respect to other versions of the system 10. The waveguides 16, 24 and 26 may be thought of as being a single waveguide with their various designations made simply for purposes of description.

Signals used in the system 10 to obtain the desired measurements may be electromagnetic radiation in the 10-0.3 mm range (30-1000 GHz range). Such electromagnetic radiation is ideally suited for remote measurements in harsh, optically unclean, and unstable processing environments. Millimeter waves have a length sufficient to penetrate optical/infrared obscured viewing paths through dust, smoke and debris. However, the wavelengths of these waves are short enough to provide spatially resolved point measurements for profile information. The system 10 may make use of a transverse electric and magnetic field mode known as an $HE_{11}$ mode. The waveguides 24 and 26 are capable of propagating the $HE_{11}$ mode through the presence of a corrugated inside surface of the waveguides 24 and 26 or with a smooth non-conducting dielectric surface. The use of the guided $HE_{11}$ mode acts to optimize coupling of the field of view launched from the end of the waveguide 26 to a diffraction limited spot size for maximum spatial resolution of the monitored surface 30. The waveguides 24 and 26 are hollow and may have an inner diameter that is larger than three times the wavelength of the signal moving therethrough. In accordance with other exemplary embodiments, the waveguides 24 and 26 may have an inner diameter that is from two to seven times the wavelength of the signal moving therethrough. The use of waveguides 24 and 26 with a diameter significantly greater than the wavelength of the signal passing therethrough makes possible small gaps between sections of the waveguides 24 and 26 without large diffractive losses in order to insert the beam splitter 18 or a chopper blade 32 in order to manipulate the resulting signals to achieve variously desired monitoring functions. The waveguides 16, 24 and 26 may be variously configured in accordance with different exemplary embodiments. For example, the waveguides 16, 24 and 26 may have tapered passageways or may have linear passageways therethrough in accordance with certain versions of the system 10.

At least a portion of the waveguide 26 is located inside of the melter 28 and thus must be capable of surviving harsh conditions present therein. The waveguide 26 may be made out of a refractory material such as inconel. Additionally or alternatively, waveguide 26 may be made out of a ceramic such as mullite so as to withstand extreme temperatures encountered in the melter 28. Components of the system 10 can be made out of the same materials as those used to construct the melter 28. The waveguides 16, 24 and/or 26 along with the transparent window 36 or other components of the system 10 can be made out of the same ceramics/alloys from which the melter 28 is constructed in order to ensure long life of the system 10. These waveguide materials have been tested and proven capable of functioning in these environments for extended periods of time.

A milliwave melter monitoring transparent window 36 is located within the passageway through the waveguide 24. The transparent window 36 can be made out of a material such as polytetrafluoroethylene or fused quartz. The transparent window 36 functions to prevent melter 28 off gasses from flowing through the waveguide 24. The transparent window 36 can be tilted at a slight angle to the axis of the passageway of the waveguide 24 in order to prevent direct reflections onto the receivers 12 and/or 14. The angle of inclination of the transparent window 36 may be varied in accordance with various exemplary embodiments. For example, the transparent window 36 may be arranged so that it is tilted at an angle from five to thirty five degrees from a perpendicular orientation to the axis of the passageway of the waveguide 24. The transparent window 36 can be treated with an antireflective coating or may have a surface structure such as a moth eye surface in order to further minimize or eliminate undesired reflections. The waveguide 24 may also include a mirror 92 or other reflective surface present within its passageway in order to desirably direct the energy transferred through the waveguide 24. However, it is to be understood that other arrangements of the waveguide 24 are possible in which the mirror 92 or other reflective surface is not present.

The milliwave melter monitoring system 10 may have, in accordance with one exemplary embodiment, a reflective chopper 32 that is rotated via a motor 34. The reflective chopper 32 functions to switch the signal back and forth between the receivers 12 and 14. The reflective chopper 32 has blades that are equal to or greater than the inside diameter of the passage of the waveguide 24 through which the signal is transmitted. The blades of the reflective chopper 32 may be room temperature or may be of a higher elevation in accordance with certain exemplary embodiments. The reflective chopper 32 may be arranged so that when a blade of the reflective chopper 32 is located within the passageway of the waveguide 24, a signal received from a location of the melter 28 such as from the monitored surface 30 is reflected to the passive receiver 14. Placement of the blade of the reflective chopper 32 is in this position likewise causes the view of the thermal return reflection receiver 12 to be blocked thus preventing the signal from reaching receiver 12. Rotation of the reflective chopper 32 so that its blade is moved out of the passageway of the waveguide 24 allows the signal from the viewed surface 30 to be directed into the receiver 12 due to the arrangement between receiver 12 and the waveguide 24. Also in this orientation, the signal will be prevented from being directed to the receiver 14 due to the placement of receiver 14 with respect to the waveguide 24. The reflective chopper 32 functions to rapidly switch the view of the viewed surface 30, and hence the signal obtained therefrom, between the thermal return reflection receiver 12 and the passive receiver 14.

The waveguides 16, 24 and 26 along with the beam splitter 18 and the reflective chopper 32 are arranged to provide a low loss quasi-optic transmission line system to interface the receivers 12 and 14 with the melter 28. The receivers 12 and 14 thus receive energy from the monitored surface 30. The transmission line uses an efficient, quasi-optical propagation mode to achieve diffraction limited resolution for spatially localized measurements. The pair of receivers 12 and 14 function to detect thermal emissions emitted and reflected by the monitored surface 30 over large bandwidths to sense temperature and emissivity thereof. The receivers 12 and 14 emit a coherent single frequency signal toward the monitored surface 30. Reflection of the coherent single frequency signals are detected by the receivers 12 and 14 in order to sense position and movement of the monitored surface 30. The use of multiple receivers, one receiver 12 to receive an actively probed thermal signal and another receiver 14 to passively receive the thermal emission, allows for both temperature and emissivity to be instantaneously determined when both of the receivers 12 and 14 are viewing the same location of the monitored surface 30. As previously stated, the monitored surface 30 is probed with a redirected fraction of the thermal emission. Thermal radiation may be used as the probe signal for emissivity measurements in order to avoid uncertainties in signal level measurements that would be caused by a coherent probe beam due to standing wave interference effects. The use of a leaked coherent probe signal naturally present when using milliwave melter monitor heterodyne receivers 12 and 14 for thermal emission measurements provides a simultaneous measurement of the monitored surface 30 position and movement due to standing wave interference effects. The use of an emitted, leaked, signal at a frequency different from the coherent, single oscillation frequency may allow for improved emissivity and location data to be obtained based upon the amplitude and phase of the returned, chopped signal.

Each one of the receivers 12 and 14 outputs a pair of signals. The passive receiver 14 outputs a thermal signal measurement 38 and a coherent probe reflection measurement 40. The thermal return reflection receiver 12 outputs a thermal signal measurement 42 and a coherent probe reflection measurement 44. The various signals 38, 40, 42 and 44 are input to a series of lock-in amplifiers. The thermal signal measurement 38 is sent to a lock-in amplifier 46, and the coherent probe reflection measurement 40 is provided to a lock-in amplifier 48. The thermal signal measurement 42 from the thermal return reflection receiver 12 is sent to a lock-in amplifier 50, and the coherent probe reflection measurement 44 is directed to a lock-in amplifier 52. The reflective chopper 32 provides a reference signal 54 to the lock-in amplifiers 46, 48, 50 and 52. In accordance with one exemplary embodiment, the reference signal 54 corresponds to the frequency at which the reflective chopper 32 rotates multiplied by the number of chopper blades. The lock-in amplifiers 46, 48, 50 and 52 function to detect signals that are synchronized to the frequency of the reflective chopper 32 in order to render the milliwave melter monitoring system 10 sensitive to small signals. Lock-in amplifier output 56 from the lock-in amplifiers 46, 48, 50 and 52 is sent to a computer 58 for processing, storage and display.

The use of efficient waveguides 16, 24 and 26 allow the location of electronic components of the system 10, such as the receivers 12 and 14, lock-in amplifiers 46, 48, 50 and 52, and computer 58 to be at locations remote from the harsh environment monitored by the system 10. For example, the electronic components may be located from twenty to two hundred feet away from the chamber of the monitored melter 28. As such, monitored processes that need to be biologically or radiologically shielded, such as nuclear waste vitrification, may be monitored by the present system from a remote location. The system 10 is robust enough to provide accurate measurements of conditions within the melter 28 without high levels of tolerance on optical elements of the system 10.

The milliwave melter monitoring system 10 is capable of obtaining measurements from the melter 28 without contacting a surface of a molten material 64 present within the melter 28. Non-contact measurements are made possible by detecting the milliwave melter monitoring emissions and reflections from a distance to the monitored surface 30. Thermal emission from the molten material 64 may be used to derive the melt temperature. The thermal reflection amplitude obtained by the system 10 can be used to determine the emissivity in the melter 28. Further, the system 10 may be capable of obtaining the surface displacement within the melter 28 without contacting the molten material 64. Combination of the temperature, emissivity, and/or surface displacement may be used in order to obtain other parameters present within the melter 28. For example, a melter foaming event can be measured through combination of the surface acceleration and emissivity in the melter 28. Additionally, an indication of salt layer formation may be detected based upon emissivity and turbulence parameters detected within the melter 28.

Further parameters within the melter 28 may be calculated based upon measurements taken without need of contacting the surface of the molten material 64. For example, the measured surface displacement may be used in order to monitor a melt pour rate within the melter 28. Further, a precise measurement of emissivity change may provide an indication of the onset of liquidus or crystal formation within the melter 28. Certain exemplary embodiments of the system 10 exist in which the only type of data obtainable from the melter 28 is through non-contact between the waveguide 26 and the molten material 64. The obtained data may be used to monitor and/or optimize a process taking place within the melter 28.

Certain exemplary embodiments provide for the ability of the system 10 to measure data in addition to the non-contact data previously discussed. The waveguide 26 may be immersed into the molten material 64 so that additional parameters such as viscosity, specific gravity and/or noble metals accumulation may be monitored. Immersion of the waveguide 26 into the molten melt 64 makes it possible to pressurize the waveguide 26 and induce a flow or displacement for viscosity and/or specific gravity measurements. The coherent reflection of the flow may be used in order to derive the viscosity of the molten melt 64. Refractory strength waveguide 26 may allow for the measurement of high-temperature viscosity of the molten material 64. The coherent reflection of displacement can be used to ascertain the specific gravity or density of the molten material 64. Contact of the molten material 64 with the waveguide 26 may result in a slight movement of the surface of the molten material 64. From the amount of displacement, it may be possible to deduce the density and viscosity of the molten material 64. Additionally, the reflection off of the metal layer below surface 30 can be used to measure the noble metal accumulation in the melter 28. Metals separation may be measured through immersion of the waveguide 26. The measured immersed waveguide 26 parameters can be obtained in addition to, or alternatively to, the non-contact measurements previously discussed. Knowledge of these additional parameters through insertion of the waveguide 26 into the molten material 64 in order to make determinations of physical properties beneath the surface of the molten material 64 allows for further monitoring and optimization of the process taking place within the melter 28.

The milliwave melter monitoring system 10 is also capable of obtaining additional measurements in accordance with still further exemplary embodiments. For example, millimeter wave radiometry can be used in order to measure plenum gas temperature above the molten material 64. Also, multiple receiver detector elements can be incorporated into the system 10 so that milliwave melter monitoring imaging of selected parameters is possible.

The waveguide 26 may be configured so as to be capable of rotating within the melter 28. In this manner, a temperature profile can be obtained with respect to multiple locations within the melter 28. Further, other properties of the melter 28 can be profiled through rotation or other movement of the waveguide 26 so as to examine various locations. The waveguide 26 may also be capable of moving or rotating when located inside of the molten material 64 so that profile information of the molten material 64 may be realized. The materials making up the waveguides 16, 24 and 26 may be robust enough such that a cooling mechanism is not present or necessary in order to keep the waveguides 16, 24 and 26 and the transparent window 36 cool or clean. Alternatively, other exemplary embodiments of the system 10 are possible in which a cooling system may be employed in which inert gas is introduced into one of the waveguides 16, 24 and 26 in order to cool the transparent window 36 or other components of the system 10 and to purge off gasses and minimize deposits.

The system 10 thus allows for the measurement of multiple parameters in the harsh environment of a melter 28. Further, the multiple parameters may be measured simultaneously in real-time using a single set of hardware. In this manner, all of the desired measurements are integrated into a single system 10 as opposed to multiple measuring devices. The system 10 can be arranged so that two or more of the previously mentioned properties can be simultaneously measured. For example, temperature and emissivity in the melter 28 can be simultaneously measured in one exemplary embodiment. In accordance with another version of the system 10, the emissivity and surface displacement can be simultaneously measured. Also, the temperature and surface displacement may be measured at the same time in accordance with another exemplary embodiment. As such, it is to be understood that the system 10 can be arranged so that the temperature, emissivity, surface displacement, foaming, salt layer formation, pour rate, liquidus, viscosity, specific gravity, and noble metal accumulation associated with the melter 28 can be simultaneously measured in any combination with one another. For instance, any combination of two, three or four of the aforementioned properties may be simultaneously measured in accordance with certain exemplary embodiments.

Figure 2:
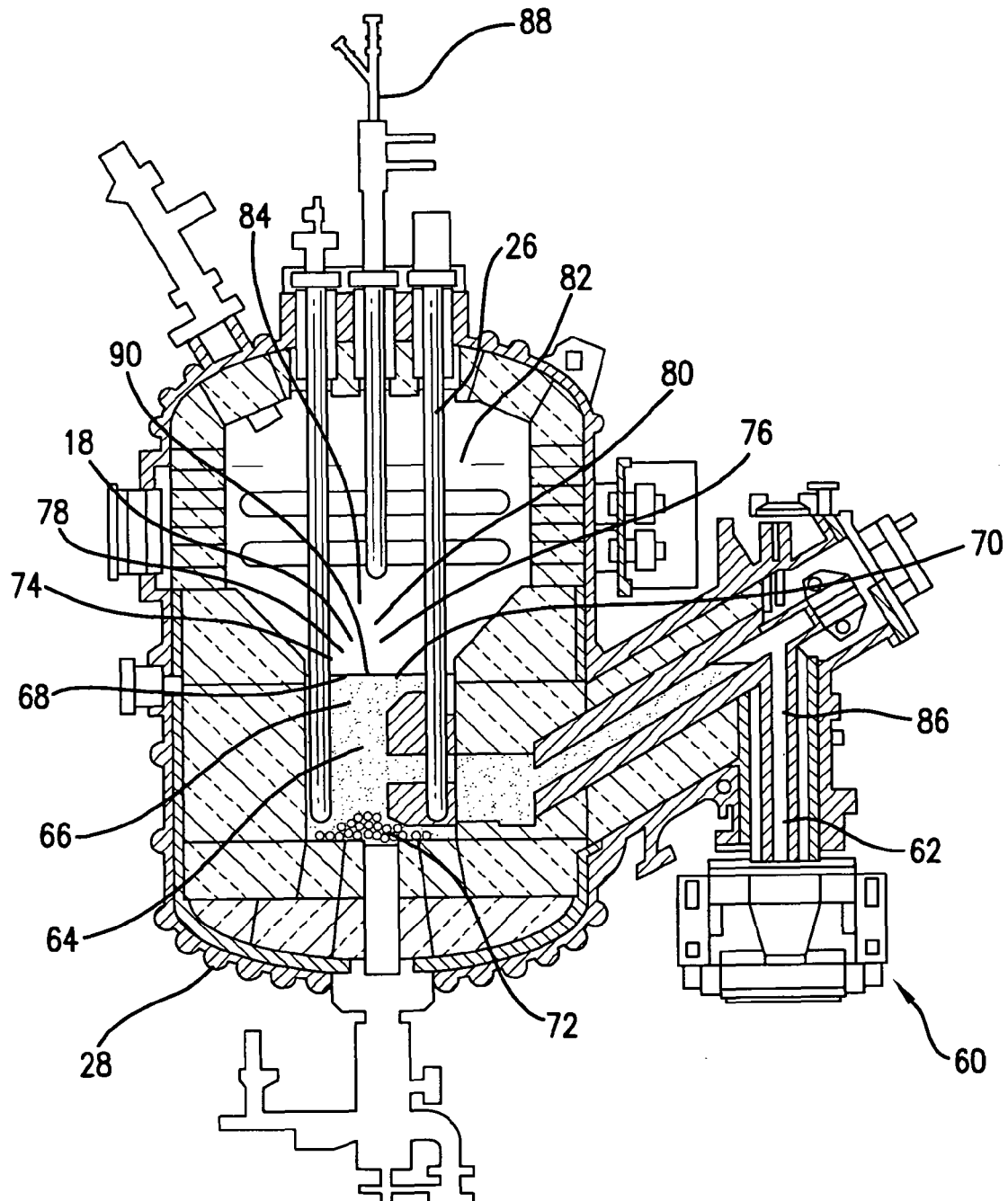
FIG. 2 is a cross-sectional view of a glass melter in which locations of various measurements taken therein are identified in accordance with one exemplary embodiment.

FIG. 2 is a cross-sectional view of a glass melter 28 that can be monitored by the milliwave melter monitoring system 10 in accordance with one exemplary embodiment. Although described as being used in combination with a glass melter 28, is it to be understood that this is only for sake of example and that the system 10 can be used with a variety of furnaces other than a glass melter 28 in other embodiments. The glass melter 28 has a feed tube 88 through which material can be introduced into the chamber of the glass melter 28. Molten material 64 is heated within the glass melter 28 and forms a cold cap 90 or crust on its upper surface at certain times within the process. Molten material can be extracted from the heating chamber through a pour spout 62 and dispensed through use of a bellows assembly 60.

As illustrated in FIG. 2, the waveguide 26 is immersed within the molten material 64. The position of the waveguide 26 may be fixed with respect to the glass melter 28, or the position of the waveguide 26 may be capable of being adjusted with respect to the melter 28 so that the waveguide 26 can be moved to various locations within the chamber of the melter 28. Placement of the waveguide 26 into the molten material 64 allows for the measurement of noble metal accumulation 72 at the position indicated in FIG. 2. Immersion also affords the system 10 the ability to measure viscosity 68 of the molten material 64 and glass density 70 at the indicated positions. Glass current/flow 66 can also be measured by the system at the position indicated within the molten material 64.

The system 10 is also capable of measuring properties within the glass melter 28 at locations remote from immersion within the molten material 64. Cold cap temperature and mapping 80 measurements may be taken at the illustrated location so that data regarding the cold cap or crust of the molten material 64 may be obtained. Salt layer formation 74, foaming and crystals formation 76, and glass emissivity/conductivity 78 may be measured at the identified locations in the cross-sectional view in FIG. 2. The plenum of the glass melter 28 includes the gasses and vapor within the chamber of the glass melter 28 that are located above the molten material 64. The system 10 may also be configured so as to monitor the plenum temperature 82 and conduct milliwave melter monitoring imaging 84 in the plenum of the glass melter 28. Additionally, the system 10 can be configured so that the glass pouring flow 86 of the liquid material is monitored at the designated location.

The milliwave melter monitoring system 10 can be used in conjunction with a glass melter 28 utilized in a process for the vitrification of nuclear waste. However, the system 10 may find utility through use in other applications. For example, the system 10 can be incorporated into furnaces or other equipment used in the manufacture of glass and ceramics, and in the refining of ores. The system 10 can be used in various high-temperature melt processes in order to increase product quality, improve processing efficiency, and reduce manufacturing costs. The system 10 enables measurements to be taken when clear views are not present and when environment being measured is otherwise visibly inaccessible.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A milliwave melter monitoring system, comprising:
a waveguide having a portion capable of contacting a molten material in a melter for use in measuring one or more properties of the molten material;
a passive receiver configured for use in obtaining signals transferred through the waveguide, wherein the passive receiver is configured for receiving signals from the waveguide when contacting the molten material for use in determining the viscosity of the molten material;
a reflection receiver capable of detecting a reflected probed signal that is directed through the waveguide to the melter and is reflected back for detection by the reflection receiver; and
a chopper that blocks signals transferred through the waveguide from reaching the reflection receiver while allowing signals transferred through the waveguide to reach the passive receiver, wherein the chopper is capable of being rotated so that signals transferred through the waveguide do not reach the passive receiver while being allowed to reach the reflection receiver such that the reflected probed signal moves past the chopper towards the melter and then is reflected to move back past the chopper to the reflection receiver.

2. The milliwave melter monitoring system as set forth in claim 1, wherein the reflection receiver is capable of detecting a coherent reflection of flow for use in determining the viscosity of the molten material, and wherein the reflection receiver is capable of detecting a coherent reflection of displacement for use in determining the specific gravity of the molten material.

3. The milliwave melter monitoring system as set forth in claim 1, wherein the reflection receiver is capable of detecting a reflection off of a noble metal layer when a portion of the waveguide contacts the molten material for use in determining noble metal accumulation in the melter.

4. The milliwave melter monitoring system as set forth in claim 1, wherein the portion of the waveguide that contacts the molten material is made of a refractory material.

5. The milliwave melter monitoring system as set forth in claim 1, wherein a portion of the waveguide is capable of being immersed into the molten material in order to induce a flow and displacement into the molten material that are capable of being detected by the reflection receiver for use in determining the viscosity of the molten material and the density of the molten material.

6. The milliwave melter monitoring system as set forth in claim 1, wherein the waveguide is capable of being located in the melter such that the waveguide does not contact the molten material, wherein signals are capable of being transferred through the waveguide for use in determining the temperature, emissivity and surface displacement in the melter.

7. The milliwave melter monitoring system as set forth in claim 6, wherein the signals transferred through the waveguide are used for determining a melter foaming event, salt layer formation, melter pour rate, and liquidus in the melter.

8. The milliwave melter monitoring system as set forth in claim 1, wherein the passive receiver is capable of detecting a thermal emission emitted from the melter and transferred through the waveguide to the passive receiver.

9. The milliwave melter monitoring system as set forth in claim 8, wherein the reflected probed signal that is directed through the waveguide to the melter is a redirected fraction of the thermal emission from the melter.

10. The milliwave melter monitoring system as set forth in claim 8, wherein the waveguide has a crossed waveguide that has a side mirror and a signal dump.

11. A milliwave melter monitoring system, comprising:
a waveguide configured for use in transferring signals;
a passive receiver capable of obtaining a signal from the waveguide that is a thermal emission;
a reflection receiver capable of obtaining a signal from the waveguide that is a reflected probed signal that is directed through the waveguide to a monitored surface and is reflected back for detection by the reflection receiver;
wherein the passive receiver and the reflection receiver are used in order to determine temperature and emissivity; and
a chopper that blocks signals transferred through the waveguide from reaching the reflection receiver while allowing signals transferred through the waveguide to reach the passive receiver, wherein the chopper is capable of being rotated so that signals transferred through the waveguide do not reach the passive receiver while being allowed to reach the reflection receiver such that the reflected probed signal moves past the chopper towards the monitored surface and then is reflected to move back past the chopper to the reflection receiver.

12. The milliwave melter monitoring system as set forth in claim 11, wherein the reflected probed signal is a redirected fraction of the thermal emission from a melter that is directed through the waveguide to the melter and reflected back from the melter for detection by the reflection receiver.

13. The milliwave melter monitoring system as set forth in claim 11, wherein the waveguide is capable of being located in a melter such that the waveguide does not contact molten material present within the melter, wherein signals are capable of being transferred through the waveguide for use in determining the temperature, emissivity and surface displacement in the melter such that resulting properties in the melter including a melter foaming event, salt layer formation, melter pour rate, and liquidus in the melter are capable of being determined.

14. The milliwave melter monitoring system as set forth in claim 11, wherein the temperature and emissivity are measured simultaneously through the use of signals obtained by the passive receiver and the reflection receiver.

15. The milliwave melter monitoring system as set forth in claim 11, wherein a portion of the waveguide is capable of contacting a molten material in a melter for use in obtaining measurements beneath the surface of the molten material, wherein the reflection receiver is capable of detecting a coherent reflection of flow for use in determining the viscosity of the molten material, and wherein the reflection receiver is capable of detecting a coherent reflection of displacement for use in determining the specific gravity of the molten material.

16. The milliwave melter monitoring system as set forth in claim 15, wherein a portion of the waveguide is capable of being moved relative to the melter so that the portion of the waveguide can be immersed within the molten material.

17. A milliwave melter monitoring system, comprising:
a waveguide configured for the transfer of signals from a melter for use in determining properties in the melter;
a passive receiver configured for receiving signals from the waveguide;
a reflection receiver configured for receiving signals from the waveguide, wherein one of the signals is a reflected probed signal that is directed through the waveguide to the melter and is reflected back for detection by the reflection receiver;

a computer configured for receiving signals from the passive receiver and the reflection receiver for use in determining temperature, emissivity, viscosity, density and a foaming event in the melter; and a chopper that blocks signals transferred through the waveguide from reaching the reflection receiver while allowing signals transferred through the waveguide to reach the passive receiver, wherein the chopper is capable of being rotated so that signals transferred through the waveguide do not reach the passive receiver while being allowed to reach the reflection receiver such that the reflected probed signal moves past the chopper towards the melter and then is reflected to move back past the chopper to the reflection receiver.

18. The milliwave melter monitoring system as set forth in claim 17, wherein a portion of the waveguide is capable of being immersed into a molten material present in a melter in order to induce a flow and displacement into the molten material that are capable of being detected by the reflection receiver for use in determining the viscosity of the molten material and the density of the molten material.

19. The milliwave melter monitoring system as set forth in claim 17, wherein the passive receiver receives a signal from the waveguide that is a thermal emission emitted from the melter, and wherein the reflection receiver detects the reflected probed signal that is a redirected fraction of the thermal emission from the melter that is directed through the waveguide to the melter and is reflected back for detection by the reflection receiver.

20. The milliwave melter monitoring system as set forth in claim 17, wherein the computer is configured for receiving signals that are used to determine plenum gas temperature in the melter, a temperature profile in the melter, and milliwave melter monitoring imaging in the melter.

\* \* \* \* \*